US006979735B1

(12) United States Patent
Booij et al.

(10) Patent No.: US 6,979,735 B1
(45) Date of Patent: Dec. 27, 2005

(54) AGGLOMERATES BY CRYSTALLIZATION

(75) Inventors: Johannes Booij, Bloemendaal (NL); Ageeth Geertruida Lefferts, Breda (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/937,834

(22) PCT Filed: Apr. 3, 2000

(86) PCT No.: PCT/EP00/02917

§ 371 (c)(1),
(2), (4) Date: Feb. 13, 2002

(87) PCT Pub. No.: WO00/41478

PCT Pub. Date: Jul. 20, 2000

(30) Foreign Application Priority Data

Apr. 1, 1999 (EP) .................................. 99201034

(51) Int. Cl.[7] ....................... C07D 503/18; A61K 9/16; A61K 31/424
(52) U.S. Cl. .................................................. 540/349
(58) Field of Search ........................ 540/355, 300–353, 540/205–230

(56) References Cited

U.S. PATENT DOCUMENTS

| | | | | |
|---|---|---|---|---|
| 3,692,781 | A | * | 9/1972 | Oughton ...................... 540/220 |
| 3,697,506 | A | * | 10/1972 | Butler ......................... 540/320 |
| 3,932,386 | A | * | 1/1976 | Nescio ........................ 540/321 |
| 4,072,569 | A | * | 2/1978 | Box ............................ 435/120 |
| 4,073,902 | A | * | 2/1978 | Scartazzini et al. ......... 514/200 |
| 4,138,555 | A | * | 2/1979 | Cook et al. ................. 540/222 |
| 4,223,006 | A | * | 9/1980 | Taskis ......................... 424/487 |
| 4,454,069 | A | * | 6/1984 | Cook et al. ................. 540/349 |
| 4,522,701 | A | * | 6/1985 | Dickakian ..................... 208/40 |
| 4,584,291 | A | * | 4/1986 | Harbridge .............. 514/210.06 |
| 4,623,855 | A | * | 11/1986 | Bulst .......................... 333/195 |
| 4,659,812 | A | * | 4/1987 | Aburaki et al. ............. 540/222 |
| 4,863,915 | A | * | 9/1989 | Ward .......................... 514/197 |
| 5,250,525 | A | * | 10/1993 | Kovacevic et al. ..... 514/210.02 |
| 5,288,861 | A | * | 2/1994 | Clark et al. ................. 540/347 |

(Continued)

FOREIGN PATENT DOCUMENTS

| | | |
|---|---|---|
| EP | 0118196 | 9/1984 |
| EP | 0277008 | 8/1988 |
| WO | WO-91/00865 | 1/1991 |
| WO | WO 9116893 | 11/1991 |
| WO | WO 9219227 | 11/1992 |
| WO | WO 9528927 | 11/1995 |
| WO | WO 9733564 | 9/1997 |
| WO | WO 9747301 | 12/1997 |
| WO | WO-98/02145 | 1/1998 |

(Continued)

OTHER PUBLICATIONS

<http://adams.allwords.com/word-random.html> Allwords.com entry for "random" dowloaded from the Internet Jun. 22, 2004.*

(Continued)

Primary Examiner—Mark L. Berch
(74) Attorney, Agent, or Firm—Morrison & Foerster LLP

(57) ABSTRACT

The present invention describes novel agglomerates in crystalline form of β-lactam compounds. Furthermore, a process for the preparation of said agglomerates, wherein a solution or suspension of at least one β-lactam compound in a solvent is mixed with one or more anti-solvents has been described.

24 Claims, 1 Drawing Sheet

U.S. PATENT DOCUMENTS

| | | | |
|---|---|---|---|
| 5,489,563 A | * | 2/1996 | Brand et al. ............... 502/185 |
| 5,869,101 A | | 2/1999 | Moller |
| 5,985,625 A | * | 11/1999 | Capuder ............... 540/349 |
| 6,417,352 B1 | * | 7/2002 | Cardoso ............... 540/349 |
| 6,440,462 B1 | * | 8/2002 | Raneburger et al. ........ 424/489 |
| 2003/0022882 A1 | * | 1/2003 | Krenmuller et al. ... 514/210.09 |

FOREIGN PATENT DOCUMENTS

| WO | WO-98/05305 | 2/1998 |
|---|---|---|
| WO | WO 9821212 | 5/1998 |
| WO | WO-99/11261 | 3/1999 |

OTHER PUBLICATIONS

Iturriaga, "A State of Sin—Pseudo-Random Numbers" <http://www.cs.utk.edu/~miturria/cs594-cns/random.html> downloaded from the Internet Jun. 22, 2004.*

Gohel et al., "Development and evaluation of a multifunctional directly compressible diluent consisting of brittle and ductile materials," Pharm. Tech., Dec. 4, 2003.*

Langer, "Existence of needle crystals in local models of solidification", Phys. Rev. A 33: 435-441.*

* cited by examiner

Figure
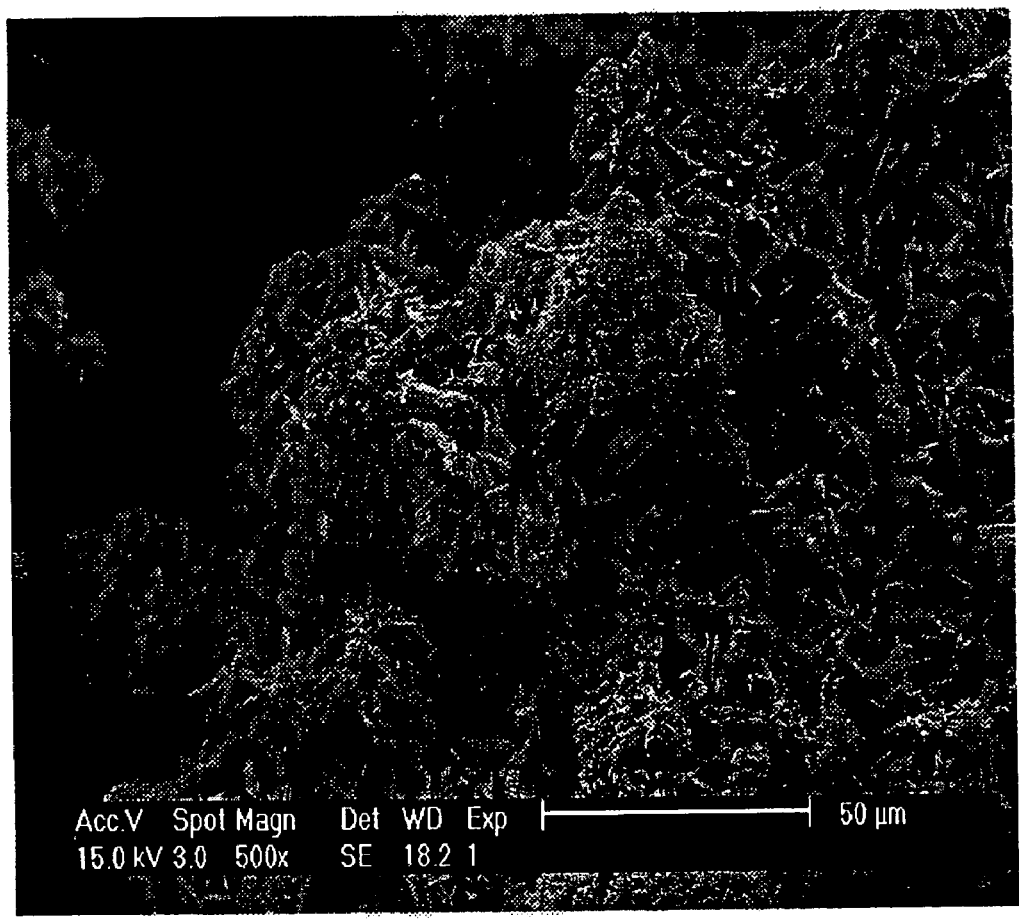

AGGLOMERATES BY CRYSTALLIZATION

FIELD OF THE INVENTION

The present invention describes agglomerates of β-lactam compounds in crystalline form and a process to prepare the same.

BACKGROUND OF THE INVENTION

β-Lactam antibiotics constitute the most important group of antibiotic compounds, with a long history of clinical use. Among this group, the prominent ones are the penicillins and cephalosporins.

Presently, most of the β-lactam antibiotics used are prepared by semi-synthetic methods. These β-lactam antibiotics are obtained by modifying a β-lactam product obtained by fermentation by one or more reactions.

Clavulanic acid and its alkaline metal salts and esters, another type of β-lactam compound than the penicillin and cephalosporin, act as β-lactamase inhibitors, able to enhance the effectiveness of penicillins and cephalosporins. Clavulanic acid has been applied therefore in pharmaceutical compositions to prevent inactivation of β-lactam antibiotics. For example, the antibacterial activity profile of amoxicillin is enhanced by the use of potassium clavulanate as β-lactamase inhibitor. A combination preparation of amoxicillin trihydrate with potassium clavulanate (Augmentin®) is well known.

It is generally known that antibiotic compounds in powder form are not suitable for formulation purposes, because generally these powders perform badly as far as flowability is concerned which causes problems in the manufacturing of final dosage forms, such as tablets. Accurate dosing of the several ingredients is needed to ensure constant end product quality. In case of poor flowabilities, such accurate dosing is difficult to guarantee. Also, the needle shaped crystals, such as of potassium clavulanate, often show a low bulk density. Thus, the contribution of such crystals to the overall volume of the final dosage form is relatively high.

To overcome these problems, often granules of compounds, for example potassium clavulanate with excipients (such as microcrystalline cellulose like Avicel® or silica like Syloid® or Aerosil®) or granules of composition, for example potassium clavulanate with other active ingredients like amoxicillin trihydrate are made before producing the final formulation. Several processes are known to form such granules. For example, in case of wet granulation, potassium clavulanate can be mixed with, for instance, amoxicillin and a binding agent after which the mixture is moistened by a solvent, granulated and bounded. Before tabletting the granules with excipients, the granulates might be sieved. This wet granulation process is economically unattractive, as it uses solvents which must be recovered and/or recycled. It is labour intensive, expensive and time consuming due to the large number of processing steps such as mixing, granulating, sieving, drying etc. Moreover, in case of unstable 1'-lactam compounds such as potassium clavulanate, wet granulation is problematic due to the use of a solvent and high temperature during the drying step of the process.

Another method to granulate poor flowing powders is dry granulation. As an example, the slugging process can be mentioned as described in International patent applications WO 9116893 and WO 9219227. Here, tablets of the poor flowing material with excipients are made and subsequently broken again and sieved to produce granules. Another example of dry granulation is the compaction process as described in International patent application WO 9528927. In this application, a process has been mentioned wherein compacted granules of a β-lactam antibiotic, for example amoxicillin, and a mixture of an active β-lactam antibiotic and a secondary pharmaceutically active agent, for example potassium clavulanate with excipients are made using roller compacting. Subsequently, the roller compacted flakes are milled, resulting in granules which can be mixed with excipients to press the final tablets. An advantage compared to the wet granulation is the absence of solvents. However, the dry granulation is relatively time consuming due to a large number of processing steps. Also, in case of unstable products, a quality risk exists due to locally high temperatures in the process, e.g. due to abrasion. In case the material is hygroscopic, such as potassium clavulanate, another disadvantage is the handling of the dried crystals before and during the granulation process. During this handling, the product might attract water leading to unwanted degradation reactions. Also a major disadvantage of roller compacted products is the relatively large amount of fines which should be removed using sieving techniques to improve the flowability of such products. Furthermore, difficulties one may encounter by using dry granulation are:

a lot of dust is produced during the slugging or roller compaction process and in some cases, for example such as amoxicillin, this dust sticks to the coarser particles and can not be separated by currently applied vibrating sieves, dust may deteriorate the flow properties of agglomerates, dust is also responsible for air born β-lactam antibiotics particles which can cause allergic reaction.

Granules of the active ingredient in the presence of excipients are produced by the process mentioned above. It would be advantageous to have the possibility to produce granules of the pure active ingredient. In that case, the production process can be more flexible and possibly overall less excipients are necessary. Also the production of final dosage forms will be more flexible. In case of hygroscopic substances such as potassium clavulanate, however, it will be difficult to granulate using one of the above processes without the presence of excipients like microcrystalline cellulose or silica, as the latter are known to protect the hygroscopic potassium clavulanate by removing the free water from it and, thus, keeping the water activity of such compositions low. However, in the International patent application WO 9733564 a method has been mentioned in which granules of a pure active ingredient, without the presence of excipients, are made by extrusion. Here, a paste is made of the crystalline powder by adding a liquid wherein the powder is insoluble or slightly soluble. The paste is kneaded then and extruded in a double screwed extruder, after which the granules are dried. The process again is not suitable for unstable products, as locally the temperature in the extruder is high (up to 80° C.). Also, this wet material should be dried at elevated temperatures.

Another method to improve the flowability of needle shaped crystals, especially in the case of potassium clavulanate, is to agglomerate them during crystallisation to the so-called rosette form as described in European patent EP 277008 B1. In this case, a plurality of needle crystals radiate out from a common nucleation point. The rosettes show an increased flowability compared to the needles. However, a large disadvantage of these types of granules is the inclusion of impurities, leading to a decreased chemical quality of the product. Also, the included impurities probably increase the degradation rate of the β-lactam compound, thus resulting in an even worse chemical quality during storage.

The object of the invention is to provide a valuable form of a β-lactam antibiotic compound and a process to prepare such a compound that overcomes most of the above mentioned disadvantages.

Surprisingly, it has been found that novel agglomerates in crystalline form of β-lactam antibiotics in a liquid phase are produced through a crystallisation process when a solution of at least one β-lactam compound in a solvent or in a mixture of solvents under stirring is mixed together with one or more anti-solvents. Preferably, one or both solutions contain water.

DESCRIPTION OF THE FIGURE

An Electron-microscope photo of potassium clavulanate agglomerates as prepared according to Example 9 is shown in the Figure.

SUMMARY OF THE INVENTION

The present invention provides agglomerates in crystalline form comprising one or more β-lactam compounds having at least one β-lactam compound of a high water affinity, and optionally contain one or more excipients. Preferably, said agglomerates comprise clavulanic acid or a pharmaceutically acceptable salt thereof like potassium clavulanate. Further, the agglomerates comprising potassium clavulanate may contain amoxicillin as the active β-lactam antibiotic compound. The term agglomerate refers to clustering of the crystals of a compound.

The excipients are microcrystalline cellulose, preferably Avicel®, or silica, preferably Syloid® or Aerosil®.

The said agglomerates can also be of sterile form.

The new agglomerates are of an average particle size between about 1 $\mu$m and 1500 $\mu$m, preferably between about 500 $\mu$m and 1500 $\mu$m, more preferably between 800 $\mu$m and 1200 $\mu$m, or between 1 $\mu$m and 300 $\mu$m, preferably between 1 $\mu$m and 200 $\mu$m.

Moreover, the agglomerates of the present invention are substantially free from non-agglomerated β-lactam crystals, for instance, non-agglomerated crystals having a weight percentage between 0–10%.

Furthermore, a process to prepare said agglomerates has been provided for. The agglomerates are produced in a liquid phase medium, which process involves mixing together a solution or suspension of at least one β-lactam compound corresponding to the β-lactam compound to be prepared in agglomerate form in a solvent or in a mixture of solvents under stirring with one or more anti-solvents, whereby at least one of both solvents and co-solvent contains water. The overall weight ratio of the solution containing the β-lactam compound to anti-solvent is about 0.05 to 10%. The solvent is for instance water or ethanol and the anti-solvent a ketone, like acetone, methylethylketone, methylisobutylketone or an ester, like methyl acetate, ethyl acetate, isopropyl acetate, butyl acetate or an alcohol, like 1-propanol, 1-butanol, 2-butanol, 2-methyl-1-propanol or a mixture of these solvents. The pH of the solution of the β-lactam compound may be adjusted to neutral. Preferably, the solvent is water or ethanol and the anti-solvent is acetone or ethyl acetate with some water present in at least the solvent or the anti-solvent. It is possible also to add other ingredients in one of the streams (solvent, anti-solvent or mixture thereof), either suspended or dissolved.

During the preparation of the agglomerates, one or more stirring devices are used to crystallise, agglomerate and deagglomerate, or to crystallise and agglomerate, or to crystallise and deagglomerate the β-lactam compound and optionally classification and blending with excipients and/or another β-lactam compound in a batch or continuous operation in one or more reaction vessels or in one integrated step. Furthermore, the operation is performed by applying stirring devices in one or more vessels, in-line mixers or a combination thereof. Furthermore, it is possible to use a high shear mixer during the preparation of these agglomerates. Also, agglomerates with various particle sizes can be prepared by using a nozzle-sprayer for the β-lactam containing solution.

The agglomerates of various particle sizes are regulated by further using a combination and permutation of different stirring devices and their speed, the type and amount of the solvents used and the way of mixing of the solvents.

Agglomerates of potassium clavulanate of the present invention show a good level of stability and hygroscopicity.

The agglomerates, prepared according to the present invention, with one or more pharmaceutical acceptable excipients are suitable for pharmaceutical formulations.

Pharmaceutical formulations comprising amoxicillin, preferably amoxicillin trihydrate and the crystalline agglomerates of potassium clavulanate of the present invention and optionally one or more pharmaceutically acceptable inert excipients form another aspect of the present invention.

Also, a pharmaceutical formulation, comprising crystalline agglomerates of amoxicillin trihydrate and potassium clavulanate and one or more pharmaceutically acceptable inert excipients can be made.

The agglomerates, prepared according to the present invention, are suitable to prepare oral dosage forms such as tablets, capsules, syrups or sachets, dry instant or ready to use in multiple or single dose form. According to another embodiment of the invention, the oral dosage form, comprising agglomerates or granules of amoxicillin with or without one or more excipients can also contain a β-lactamase inhibitor such as potassium clavulanate, preferably in the agglomerated form. Said agglomerates can also be used in Dose Sipping devices.

DETAILED DESCRIPTION OF THE INVENTION

The present invention provides economically interesting agglomerates in crystalline form of a β-lactam compound. The β-lactam compounds are for instance clavulanic acid but one can also think of amoxicillin or ampicillin. The compound can be in the salt form, such as amine or alkaline metal salt. Preferably, agglomerates of potassium clavulanate are produced.

The agglomerates of said invention have an average particle size between about 1 $\mu$m and 1500 $\mu$m, preferably between about 500 $\mu$m and 1500 $\mu$m, more preferably between 800 $\mu$m and 1200 $\mu$m, or between 1 $\mu$m and 300 $\mu$m, preferably between 1 $\mu$m and 200 $\mu$m.

Furthermore, said agglomerates are preferably substantially free from non-agglomerated β-lactam crystals, as for instance in the needle form. By substantially free from non-agglomerated crystals is meant that the agglomerates have a weight percentage between 0–10% of non-agglomerates.

A process for the preparation of the agglomerates, wherein one or more β-lactam compounds with or without excipients are used, consists of a crystallisation procedure to build up agglomerates. The process comprises mixing together a solution or suspension of one or more β-lactam compounds corresponding to the agglomerates to be produced in a solvent or in a mixture of solvents with one or more anti-solvents under stirring. The combination of solvent and anti-solvent can result in an emulsion. In the solvent or anti-solvent an amount of water should be present, for instance in an amount of 0.05 to 10%. Thereafter, the agglomerates are filtered off, washed and dried. The agglomerates, thus produced in high yield, maintain the quality criteria set and are highly suitable for further processing. For the present application, a anti-solvent is defined as a liquid in which the β-lactam compound does not dissolve or dissolves only poorly.

More in detail, the β-lactam compound, for instance potassium clavulanate, is dissolved or suspended in an appropriate solvent or a mixture of (partly) miscible solvents, such as water, alcohols, like ethanol, methanol, 1-propanol, 2-butanol, 2-methyl-propanol, ketones, like acetone, methylethylketone, methylisobutylketone, or an ester, like methyl acetate, ethyl acetate, butyl acetate, with at least a small amount of water present. Sometimes an emulsion is formed during the agglomeration process. Optionally, the pH of the solution is adjusted to about neutral, namely to pH 5.0–7.5 by adding an acid, as for instance acetic acid or ethylhexanoic acid. The way of dissolution will be known to those skilled in the art and will depend on the stability of the β-lactam compound in the solvent or in a mixture of solvents. In case water is used as the only solvent for the dissolution of potassium clavulanate, residence time and temperature should be as low as possible and a technique such as in-line mixing, for example a static mixer, can be attractive. If for example acetone is present, a residence time of several hours might be acceptable.

The β-lactam compound, for example potassium clavulanate, present in the solvent dissolved or in suspension or in both forms, is contacted with a anti-solvent such as ketone, like acetone, methylethylketone, methylisobutylketone, or an ester, such as methyl acetate, ethyl acetate, butyl acetate or a mixture thereof, or an alcohol such as 1-propanol, 2-butanol, 2-methyl-propanol optionally containing a solvent for the β-lactam compound, such as water or an alcohol, like methanol or ethanol for potassium clavulanate. The overall weight ratio of the solution containing the β-lactam compound to the anti-solvent depends on the combination of solvents and on the desired agglomerate diameter, but generally lies within 0.05–10%. Also, it is possible to adjust this ratio by adding some solvent to the crystalliser before or during the process. This ratio will influence the average diameter of the agglomerates: the higher the relative volume of the solvent, the larger the agglomerates will be.

Several methods of mixing can be applied and will be known to those skilled in the art. For example, the solution of the β-lactam compound, for instance a potassium clavulanate solution and the anti-solvent can be added simultaneously to the crystalliser or the solution of the β-lactam compound, for instance a potassium clavulanate solution can be added to the anti-solvent or the anti-solvent can be added to the solution of the β-lactam compound, for instance a potassium clavulanate solution. The temperature should be kept below 50° C. The use of seeding material can also be advantageous to enhance the agglomeration process.

The method of contacting the potassium clavulanate containing solution and the anti-solvent can be controlled via specific equipment, such as spray nozzles or capillaries. This contacting can occur in a vessel or in line or in a recycling loop over the vessel. It is also possible to first form droplets of solution of a certain diameter, after which the droplets are contacted with the anti-solvent.

Parameters such as the amount of nozzles, their diameter, the flow through the nozzles and the rotational speed of the mixer can be used to control the average particle size and density. In this way, several grades of agglomerates can be produced, with different physical properties.

The method of agitation is determined by the desired agglomeration size of the β-lactam compound. In case of relatively large agglomerates (order of magnitude of 1000 μm), the agitation should be moderate. For example a common turbine agitator or pitched blade agitator can be used. Here, the general scales up parameters for agitation apply: the diameter of the blades versus the diameter of the vessel should be between 0.2–0.9, preferably between 0.2–0.5, depending on the type of agitator used. The rotational speed (and thus shear), tip velocity, the size of the nozzle sprayer and power input determine the agglomerate size and density and can be used as control parameters. In case the desired agglomerate diameter is small, for example 50–100 μm, high speed agitators, such as toothed disks or rotor-stator mixers with multiple stage mixing/shearing action can be used. It is also possible to use in-line high shear mixers, with the advantage of short residence times. If needed, a recycle loop can be applied over such an in-line system. Another possibility is to combine a moderate shear mixer with a high shear mixer or a mill. For example, agglomerates with a diameter of the order of a magnitude of 1000 μm can be deagglomerated during the crystallisation using a high shear mixer, which is situated in the same crystalliser (such as mounted in the bottom) or as a separate unit after the crystalliser. Also, for example a colloid mill can be placed after the crystalliser for the same purpose. Moreover, the simultaneous crystallisation/agglomeration technique can be combined using ultrasonic crystallisation. This technique has been described for instance in *Pharmaceutical Technology Europe,* 9(9), 78 (1997). In this way different grades concerning particle size distribution, density, porosity and flowability can be easily achieved.

Generally, the residence time in the crystalliser and/or deagglomerator is determined by the desired average diameter of the agglomerates. For purposes of precipitation/crystallisation, long ageing times are not needed, as the crystals are formed immediately after contact with the anti-solvent. For agglomeration and deagglomeration, however, a certain minimum and maximum residence time will be valid, depending on parameters such as mixing time and volume of the vessel.

One of the embodiments of the invention is to have the excipients included in the agglomerates by addition of the same before, after or during the precipitation and/or agglomeration, such as cellulose, preferably microcrystalline cellulose, more preferably with a water activity <0.2 at 25° C., most preferably Avicel® PH112. Also, amorphous silica (Syloid®) or colloidal silicon dioxide (Aerosil®) can be used as excipient. All methods of mixing are possible: for example the excipient can be added before, simultaneously or after the addition of the β-lactam compound solution or (partly) suspension to the crystalliser. The excipients can be added as dry matter, suspended or dissolved in a solvent, preferably one of the solvents (or a mixture thereof) which is already used in the agglomeration process. An extra advantage of the addition of such excipients is the positive influence on the agglomeration formation, as they can act as some kind of seeding material.

Another embodiment of the present invention is that the crystallisation and agglomeration can occur in the presence of another active β-lactam ingredient, for example amoxicillin trihydrate besides potassium clavulanate. The amoxicillin can either be added as a solution or suspension leading to co-crystallisation, similar to the agglomeration in the presence of excipients.

The agglomerates of the present invention are not of the rosette type: they consist of small crystals clustered together in a random order (see the Figure). Depending on the method of agitation, method of addition and amount of water, the agglomerate size can easily be adjusted between about 1 and 1500 μm and also relatively small particles as with an average size of 100 μm or relatively large particles with an average size of 1000 μm may be prepared. Compared to, for example, dry compaction, the amount of fines that either must be discharged of or that must be recycled, is small. The agglomerates can easily be separated by for example, filtration or centrifugation and subsequently dried using conventional methods such as tumbling drying. It is also possible to include a classification process. For example, agglomerates of the desired size can be selectively removed from the crystalliser using gravity and/or a sieve. Fines or large particles which can be removed by sieving as well, can be recycled, either by addition in suspension or solution to the next batch.

If necessary, pH-adjustment in order to adapt the pH of the end product can be achieved by adding an acid or base to the solution or the anti-solvent before contacting the streams of solvents containing the β-lactam compound and the anti-solvent. Also, acid or base can be added during the precipitation/crystallisation/ agglomeration process or even after the process.

Surprisingly, the process of the present invention produces agglomerates with a high bulk density, an improved flowability and less compressibility, which can be regulated. For example, potassium clavulanate agglomerates produced can have a loose bulk density between about 0.20 and 0.60 and a tapped bulk density between about 0.50 and 0.90 g/ml and a compressibility between about 10 and 40%.

Due to the excellent flowability of the agglomerates prepared using the above method, they can be used for, for example, direct compression of tablets without the need for further pre-granulation. Moreover, due to the decreased surface area of the agglomerates, the degradation caused by chemical reactions on the surface (e.g. with water) may be reduced. The level of impurities in the agglomerates is also equal to or even lower than in case of conventional needles type crystals. As the bulk density increases significantly, large advantages can be achieved in the transportation as well as in the tabletting process: the final tablet volume can decrease significantly when using agglomerates compared to using needles.

The energy consumption of the present process is low, as the crystallisation process which is commonly present in the down stream process of pharmaceuticals can be combined with the agglomeration process. Moreover, it is possible to combine the usual operations comprising purification and separation by precipitation or crystallisation, agglomeration and deagglomeration, classification and blending with e.g. excipients in one unit. The temperatures can be kept below 50° C. during the complete agglomeration process, excipients-free agglomerates can be produced and handling of dry solids before the granulation does not occur, which is an important advantage in case of hygroscopic materials. The solvents needed for the agglomeration can easily be recycled, possibly without the need for purification. Moreover, the possibility to make pure agglomerates of an unstable and hygroscopic product such as potassium clavulanate is highly attractive.

The agglomerates of the present invention can be used for all formulations to produce chew, swallow, disperse, effervescent or normal tablets of all sizes, forms and weights, also to fill hard gelatine capsules and to formulate dry syrups and for administering drugs with the help of a dose sipping device. These agglomerates can also be used, for instance, in a pharmaceutical composition as a tablet of amoxicillin trihydrate produced from agglomerates of amoxicillin trihydrate and potassium clavulanate. For the preparation of sterile agglomerates, the solution of the β-lactam compounds, solvent and anti-solvent are sterilely filtered prior to crystallisation/agglomeration. Also, the sterile agglomerates substantially free of non-agglomerates, form another aspect of the present invention.

The invention will now be described with reference to the following Examples, which are not to be constructed as being limiting on the invention, and are provided purely for illustrative purposes.

EXAMPLE 1

Preparation of Agglomerates of Potassium Clavulanate (Batch Process).

In a 5-liter flask equipped with a mechanical stirrer, a thermometer and inlet for nitrogen, 4 liters of acetone were placed. A solution of potassium clavulanate (60 g.) in a mixture of water/acetone (120 g, 1:1 w/w) was added in 30 min at 20° C. under stirring.

The solid material was filtered off and dried in vacuum at 30° C. during 2–3 hours to give agglomerates of potassium clavulanate with an average diameter in the range of 100–1000 μm and a yield of 98%.

EXAMPLE 2

Preparation of Agglomerates of Potassium Clavulanate (Semi-Continuous Process).

In a 2-liter flask equipped with a mechanical stirrer, a thermometer and inlet for nitrogen, acetone (1000 ml) and water (10 ml) were placed. Simultaneously a solution of potassium clavulanate (60 g) in a mixture of water/acetone (120 g, 1:1 w/w) and acetone (4000 ml) was added in about one hour, while agitating.

During the addition the content of the vessel was kept at about 1800 ml by periodically removing suspension through an outlet. Thereafter, the solid material was filtered off, washed with dry acetone and dried in vacuum at 30° C. during 2–3 hours to yield potassium clavulanate agglomerates with an average diameter in the range of 500–1500 μm.

EXAMPLE 3

Preparation of Agglomerates of Potassium Clavulanate by using a Turbine Stirrer Without Baffles in the Reaction Vessel.

Acetone (300 ml) and water (3 ml) were placed in a glass cylinder (100 mm in diameter, 150 mm height) equipped with a turbine stirrer (40 mm diameter), a two dropping funnel and a nitrogen inlet tube. Under stirring (900 rpm) simultaneously a solution of potassium clavulanate (30 g) in a water/acetone mixture (60 g, 1:1 w/w) and acetone (2000 ml) were added.

During the addition, the contents of the vessel were kept at about 900 ml by removing a part of the contents with the help of an outlet. After the completion of the additions, the solid material was filtered off, washed with dry acetone and dried in vacuum at 30° C. Agglomerates of potassium clavulanate with an average particle diameter of 1000 μm were obtained in 98% yield.

EXAMPLE 4

Preparation of Agglomerates of Potassium Clavulanate by using Turbine Stirrer with Baffles in the Reaction Vessel.

The experiment was repeated as described in Example 3, but using a vessel with four baffles with a width of 10 mm. Potassium clavulanate agglomerates with an average diameter in the range of 500–1000 μm were obtained.

EXAMPLE 5

Preparation of Agglomerates of Potassium Clavulanate by using a Ultra-Turrax Mixer.

Acetone (500 ml) and water (5 ml) were placed in an one liter 4-necked round-bottom flask equipped with a thermometer, Ultra-Turrax mixer (type T25 and shaft S25N-18G), two dropping funnels and a nitrogen inlet tube.

Under mixing (8000 rev/min) simultaneously a solution of potassium clavulanate (30 g.) in a water/acetone mixture (60 g. 1:1 w/w) and acetone (2000 ml) was added in one hour at 15–20° C. During the addition, the contents of the vessel were kept between 700 and 800 ml by removing a part of the content with the help of an outlet.

After the completion of the additions, the solid material was filtered off, washed with acetone and dried in vacuum at 30° C. Agglomerates of potassium clavulanate with an average diameter in range of 50–250 μm were obtained.

EXAMPLE 6

Preparation of Agglomerates of Potassium Clavulanate by using Silverson L4RT Mixer.

The experiment was repeated as described in Example 5, but using a rotor-stator type high shear mixer (Silverson mixer with emulsion screen, i.e. a screen with spherical pores of about 1.5 mm) at 3000 rev/min.

Agglomerates of potassium clavulanate with an average diameter in the range of 10–200 μm were obtained.

EXAMPLE 7

Preparation of Agglomerates of Potassium Clavulanate in Ethyl Acetate.

Ethylacetate (400 ml) and water (1 ml) were placed in a glass cylinder (100 mm in diameter, 150 mm height) equipped with a turbine stirrer (40 mm diameter), a two dropping funnel and a nitrogen inlet tube. Under stirring (900 rpm) at the same time a solution of potassium clavulanate (10 g) in water (10 ml) and ethyl acetate (600 ml) were added.

After the completion of the additions the solid was filtered off, washed with dry ethyl acetate and dried in vacuum at 30° C. to give agglomerates with an average diameter in the range of 500–1500 μm.

EXAMPLE 8

Comparison of Agglomerates and Needles of Potassium Clavulanate, Optionally Mixed with Avicel PH112.

The agglomerates of potassium clavulanate were prepared as described in Example 6, but using a Silverson mixer with general purpose disintegrating screen, i.e. a screen with square holes with a diameter of about 2.5 mm. In a 2- liter flask equipped with the Silverson mixer, a thermometer and inlet for nitrogen acetone (1000 ml) and water (10 ml) were placed. Under mixing (3400 rev/min) simultaneously a solution of potassium clavulanate (120 g) in a mixture of water/acetone (240 g, 1:1 w/w) and acetone (8000 ml) were added at 15–20° C. During the addition the contents of the vessel was kept at about 1800 ml with an outlet. After completion of the additions the solid was filtered off, washed with acetone and dried in vacuum at 30° C. during 2–3 hours to give agglomerates with an average diameter in the range of 40–200 μm.

Needles of potassium clavulanate were prepared by suspending diclavulanate salt of bis(2-dimethylaminoethyl) ether (100 g) in acetone (3350 ml) and water (50 ml). Under stirring a solution of potassium 2-ethylhexanoate (1450 ml, 0.34 M) in acetone at 5–10° C. was added. After 1 hour stirring the mixture was filtered off, washed with dry acetone and dried in vacuum during 18 hours at room temperature to give 81.2 g of potassium clavulanate needles.

A comparison of physical properties of potassium clavulanate in agglomerated and needle form, optionally mixed with Avicel PH12 in a ratio of 70: 30 w/w % have been described in Table 1.

TABLE 1

Comparison of physical properties of potassium clavulanate in agglomerated and needle form, optionally mixed with Avicel PH112

| Material | Loose bulk density | Tapped bulk density | Compressibility | Particle size distribution |
|---|---|---|---|---|
| Agglomerates of potassium clavulanate | 0.49 g/ml | 0.68 g/ml | 28% | between 1 and 200 μm |
| Needles of Potassium clavulanate | 0.18 g/ml | 0.36 g/ml | 50% | between 5 and 75 μm |
| Agglomerates of potassium clavulanate mixed with Avicel PH112 | 0.43 g/ml | 0.61 g/ml | 29% | Not determined |
| Needles of potassium clavulanate mixed with Avicel PH112 | 0.20 g/ml | 0.40 g/ml | 50% | Not determined |

EXAMPLE 9

Preparation of Agglomerates of Potassium Clavulanate in Acetone/Water at a Speed of the Agitator of 3000 RPM.

A solution of potassium clavulanate was made by dissolving circa 5 kg of potassium clavulanate in 10 l aqueous acetone (acetone:water=50:50 w/w). This solution, which was kept at 5° C. was pumped through a 0.9 mm nozzle to a crystalliser equipped with a high shear mixer and containing 50 l of acetone. Simultaneously, acetone was added to the crystalliser with a volume ratio compared to the solution of circa 21. During the process, the rotational speed of the agitator was 3000 RPM and the temperature was circa 15° C. The agglomerated suspension was removed continuously from the crystalliser, centrifuged, washed with dry acetone and dried in vacuum at 30° C. In this way, agglomerates such as shown on the Figure were produced with a loose bulk density of 0.22 g/ml, a tapped bulk density of 0.30 g/ml and a compressibility of 27%. The particle size distribution is given in Table 2 and a photo made by an Electron-microscope of potassium clavulanate is shown in the Figure.

TABLE 2

| Particle size distribution [volume %] | | | | | |
|---|---|---|---|---|---|
| <75 μm | 75–150 μm | 150–250 μm | 250–500 μm | 500–710 μm | >710 μm |
| 46.3 | 43.3 | 8 | 1 | 0.2 | 0.1 |

EXAMPLE 10

Influence of the Agitator Speed during Agglomeration on the Physical Properties of the Agglomerates.

A solution of potassium clavulanate was made by dissolving circa 10 kg of potassium clavulanate in 20 l aqueous acetone (acetone:water=50:50 w/w). This solution, which was kept at 5° C. was pumped through a 2.5 mm nozzle to a crystalliser equipped with a high shear mixer and containing 40 l of acetone. Simultaneously, acetone was added to the crystalliser with a volume ratio compared to the solution of circa 22. During the process, the rotational speed of the agitator was increased from 1000 RPM to 2000 RPM and the temperature was circa 15° C. Continuously, the suspension was removed from the crystalliser using a pump. The two agglomerated suspensions made were centrifuged, washed with dry acetone and dried in vacuum at 30° C. The physical properties can be seen in Table 3.

EXAMPLE 11

Influence of the Flow Upon Addition to Crystalliser on the Physical Properties of the Agglomerates.

Two experiments were performed in which all parameters were kept constant, except the flows of the solution and acetone to the crystalliser. In both experiments, a solution of potassium clavulanate was made by dissolving circa 5 kg of potassium clavulanate in 10 l aqueous acetone (acetone:water= 50:50 w/w). This solution, which was kept at 5° C. was pumped through a 0.9 mm nozzle to a crystalliser equipped with a high shear mixer and containing 30 l of acetone. Simultaneously, acetone was added to the crystalliser with a volume ratio compared to the solution of circa 21. During the process, the rotational speed of the agitator was 3000 and the temperature was circa 15° C. In the first experiment, the solution flow was 15 l/h and the acetone flow was 312 l/h. In the second experiment, the flows were decreased by A factor 2. Continuously, the suspension was removed form the crystalliser using a pump. The two agglomerated suspensions made were centrifuged, washed with dry acetone and dried in vacuum at 30° C. The physical properties can be seen in Table 4.

TABLE 4

| | | | | Physical properties: Particle size distribution [volume %] | | | | | |
|---|---|---|---|---|---|---|---|---|---|
| | Loose bulk density [g/ml] | Tapped bulk density [g/ml] | Compressibility [%] | <75 μm | 75–150 μm | 150–250 μm | 250–500 μm | 500–710 μm | >710 μm |
| High flow | 0.27 | 0.36 | 25 | 48.7 | 41.2 | 9.3 | 0.3 | 0 | 0 |
| Low flow | 0.35 | 0.44 | 20 | 48.8 | 50.4 | 1.1 | 0.6 | 0.4 | 0 |

EXAMPLE 12

Influence of the Nozzle Diameter Through which the Potassium Clavulanate Solution is Pumped on the Physical Properties of the Agglomerates.

Two experiments were performed in which all parameters were kept constant, except the diameter of the nozzle through which the potassium clavulanate solution is added to the crystalliser. In both experiments, a solution of potassium clavulanate was made by dissolving circa 5 kg of potassium clavulanate in 10 l aqueous acetone (acetone:water=50:50 w/w). This solution, which was kept at 5° C., was pumped through either a 0.9 mm or 1.2 mm nozzle to a crystalliser equipped with a high shear mixer and containing 50 l of acetone. Simultaneously, acetone was added to the crystalliser with a volume ratio compared to the solution of circa 21. During the process, the rotational speed of the agitator was 3000 and the temperature was circa 15° C.

TABLE 3

| | | | | Physical properties: particle size distribution [volume %] | | | | | |
|---|---|---|---|---|---|---|---|---|---|
| | Loose bulk density [g/ml] | Tapped bulk density [g/ml] | Compressibility [%] | <75 μm | 75–150 μm | 150–250 μm | 250–500 μm | 500–710 μm | >710 μm |
| 1000 RPM | 0.39 | 0.44 | 11 | 5.1 | 6.5 | 20.7 | 60.8 | 6.1 | 0.2 |
| 2000 RPM | 0.42 | 0.47 | 11 | 1.8 | 2.4 | 9.5 | 57.3 | 27 | 1.5 |

Continuously, the suspension was removed from the crystalliser using a pump. The two agglomerated suspensions made were centrifuged, washed with dry acetone and dried in vacuum at 30° C. The physical properties can be seen in Table 5.

TABLE 5

Physical properties: particle size distribution [volume %]

| Nozzle diameter | Loose bulk density [g/ml] | Tapped bulk density [g/ml] | Compressibility [%] | <75 $\mu$m | 75–150 $\mu$m | 150–250 $\mu$m | 250–500 $\mu$m | 500–710 $\mu$m | >710 $\mu$m |
|---|---|---|---|---|---|---|---|---|---|
| 0.9 mm | 0.22 | 0.3 | 0.27 | 46.3 | 43.3 | 8 | 1 | 0.2 | 0.1 |
| 1.2 mm | 0.36 | 0.44 | 0.18 | 15.9 | 50.6 | 31.3 | 1.9 | 0 | 0.3 |

What is claimed is:

1. A process for preparing an agglomerate of potassium clavulanate, comprising;
   a) dissolving or suspending a potassium clavulanate crystal in a solvent or mixture of solvents in the presence of water to form a solution or suspension;
   b) contacting said solution or suspension with an anti-solvent using a nozzle sprayer and under stirring using a stirring device
   thereby precipitating an agglomerate of potassium clavulanate having a weight percentage of between 0% and 10% potassium clavulanate crystals in the needle form, and with the proviso that the rosette-like crystalline form of potassium clavulanate is excluded.

2. A process according to claim 1, wherein the ratio of the weight of the solution containing the potassium clavulanate to the anti-solvent is about 0.05 to 10 wt. %.

3. A process according to claim 1, wherein the solvent is water, ethanol, or a mixture thereof.

4. A process according to claim 1, wherein the anti-solvent is a ketone, an ester, or an alcohol, or a mixture thereof, optionally containing water.

5. A process according to claim 1, wherein the stirring is performed by applying stirring devices in one or more vessels, in-line mixers or a combination thereof.

6. A process according to claim 5, wherein the stirring device is a high shear mixer.

7. A process according to claim 1, wherein said stirring is performed by combining and permuting different stirring devices, the speeds of said devices, the type and amount of the solvents used, and mixing one or more solvents and anti-solvents.

8. A process according to claim 1, wherein the agglomerate has an average particle size between about 1 $\mu$m and 1500 $\mu$m.

9. A process according to claim 1, wherein the process comprises dissolving the potassium clavulanate in a solvent, adjusting the pH to about neutral and mixing with the anti-solvent.

10. A process according to claim 8, wherein the agglomerate has an average particle size about 100 $\mu$m.

11. A process according to claim 8, wherein the agglomerate has an average particle size about 1000 $\mu$m.

12. A process according to claim 1, wherein the agglomerate has a bulk density between about 0.20 g/mL and 0.60 g/mL.

13. A process according to claim 1, wherein the agglomerate has a compressibility between about 10% and 40%, calculated as 100 times the ratio of the difference between tapped bulk density and loose bulk density to the tapped bulk density.

14. A process according to claim 1, wherein the agglomerate further comprises amoxicillin.

15. A process according to claim 1, wherein the agglomerate optionally contains one or more excipients.

16. A process according to claim 15, wherein the one or more excipients are selected from the group consisting of microcrystalline cellulose and silica.

17. The process of claim 1, wherein the solvent is aqueous acetone.

18. A process for preparing potassium clavulanate in the form of an agglomerate, comprising contacting a potassium clavulanate crystal in water or ethanol in the presence of water, and contacting the resulting solution with an anti-solvent using a nozzle sprayer and under stirring using a stirring device to cause precipitation of an agglomerate comprising potassium clavulanate,
   wherein said agglomerate has a weight percentage of between 0% and 10% potassium clavulanate crystals in the needle form, and with the proviso that the rosette-like crystalline form of potassium clavulanate is excluded.

19. The process of claim 18, wherein the potassium clavulanate in water further comprises acetone.

20. The process of claim 18, wherein said anti-solvent is acetone or ethyl acetate.

21. The process of claim 1, wherein said solution or suspension is pumped through said nozzle to a vessel containing said antisolvent.

22. The process of claim 21, wherein said vessel is equipped with a stirring device.

23. The process of claim 22, wherein said stirring device is a high shear mixer.

24. The process of claim 21, wherein an additional portion of antisolvent is simultaneously added to the vessel.

* * * * *

UNITED STATES PATENT AND TRADEMARK OFFICE
CERTIFICATE OF CORRECTION

PATENT NO. : 6,979,735 B1
DATED : December 27, 2005
INVENTOR(S) : Johannes Booij et al.

It is certified that error appears in the above-identified patent and that said Letters Patent is hereby corrected as shown below:

Title page,
Item [54], Title, should read -- AGGLOMERATES BY CRYSTALLISATION --.
Item [73], Assignee, should read -- DSM IP ASSETS B.V., (Heerien (NL) --.

Signed and Sealed this

Twenty-eighth Day of February, 2006

JON W. DUDAS
*Director of the United States Patent and Trademark Office*

UNITED STATES PATENT AND TRADEMARK OFFICE
CERTIFICATE OF CORRECTION

PATENT NO. : 6,979,735 B1
DATED : December 27, 2005
INVENTOR(S) : Johannes Booij et al.

It is certified that error appears in the above-identified patent and that said Letters Patent is hereby corrected as shown below:

<u>Title page,</u>
Item [54], Title, should read -- AGGLOMERATES BY CRYSTALLISATION --.
Item [73], Assignee, should read -- DSM IP ASSETS B.V., (Heerlen (NL) --.

This certificate supersedes Certificate of Correction issued February 28, 2006.

Signed and Sealed this

Twenty-third Day of May, 2006

JON W. DUDAS
*Director of the United States Patent and Trademark Office*